US012765847B2

(12) United States Patent
Wrege et al.

(10) Patent No.: US 12,765,847 B2
(45) Date of Patent: Oct. 20, 2026

(54) CT DETECTOR MODULE AND CT DEVICE

(71) Applicant: Siemens Healthineers AG, Forchheim (DE)

(72) Inventors: Jan Wrege, Erlangen (DE); Miguel Labayen De Inza, Forchheim (DE); Robert John Ellwood, Erlangen (DE); Stefan Woelfel, Dormitz (DE)

(73) Assignee: Siemens Healthineers AG, Forchheim (DE)

( * ) Notice: Subject to any disclaimer, the term of this patent is extended or adjusted under 35 U.S.C. 154(b) by 194 days.

(21) Appl. No.: 18/748,683

(22) Filed: Jun. 20, 2024

(65) Prior Publication Data

US 2024/0427032 A1 Dec. 26, 2024

(30) Foreign Application Priority Data

Jun. 22, 2023 (EP) .................................... 23180925

(51) Int. Cl.

| | |
|---|---|
| ***A61B 6/03*** | (2006.01) |
| ***A61B 6/00*** | (2006.01) |
| ***A61B 6/42*** | (2024.01) |
| ***G01T 1/20*** | (2006.01) |
| ***G01T 1/24*** | (2006.01) |

(52) U.S. Cl.

CPC ............ *A61B 6/035* (2013.01); *A61B 6/4233* (2013.01); *A61B 6/4488* (2013.01); *G01T 1/20182* (2020.05); *G01T 1/20188* (2020.05); *G01T 1/243* (2013.01); *G01T 1/244* (2013.01)

(58) Field of Classification Search

None

See application file for complete search history.

(56) References Cited

U.S. PATENT DOCUMENTS

| | | | | |
|---|---|---|---|---|
| 7,586,095 B2 * | 9/2009 | Lutz | A61B 6/035 | 250/370.09 |
| 7,626,173 B2 * | 12/2009 | Hackenschmied | G01T 1/2985 | 250/363.08 |
| 8,536,552 B2 * | 9/2013 | Freund | G01T 1/1648 | 250/397 |
| 8,710,448 B2 * | 4/2014 | Luhta | H10F 39/1898 | 257/446 |
| 8,829,446 B2 * | 9/2014 | Abenaim | G01T 1/2985 | 250/363.01 |

(Continued)

FOREIGN PATENT DOCUMENTS

| | | |
|---|---|---|
| DE | 102006025764 B4 | 7/2008 |
| DE | 102007033463 A1 | 1/2009 |

OTHER PUBLICATIONS

English translation of DE 10 2007 033 463 A1, cited in the IDS filed Jun. 20, 2024 (Year: 2009).*

*Primary Examiner* — Thomas R Artman
(74) *Attorney, Agent, or Firm* — Harness, Dickey & Pierce, P.L.C.

(57) ABSTRACT

A CT detector module comprises at least one X-ray converter element which has an upper side and a lower side. At the upper side, the X-ray converter element has an X-ray detector layer, and at the lower side the X-ray converter element is secured to a heat-conducting module carrier. The X-ray converter element is in heat-conducting contact with at least one metal element, and the at least one metal element is in heat-conducting contact with the module carrier.

20 Claims, 5 Drawing Sheets

(56) References Cited

U.S. PATENT DOCUMENTS

| | | | | |
|---|---|---|---|---|
| 9,907,523 | B2 * | 3/2018 | Hofmann | A61B 6/4233 |
| 10,307,117 | B2 * | 6/2019 | Park | A61B 6/56 |
| 10,488,532 | B2 * | 11/2019 | Abenaim | G01T 1/20184 |
| 11,029,423 | B2 * | 6/2021 | Onouchi | G01T 1/241 |
| 11,067,707 | B2 * | 7/2021 | Crestani | G01T 1/243 |
| 2006/0200976 | A1 * | 9/2006 | Freund | H01R 13/6485 29/825 |
| 2007/0278412 | A1 | 12/2007 | Hackenschmied et al. | |
| 2007/0280410 | A1 * | 12/2007 | Lutz | A61B 6/4488 378/19 |
| 2009/0121146 | A1 * | 5/2009 | Luhta | H10F 39/1898 250/370.11 |
| 2012/0132833 | A1 * | 5/2012 | Freund | G01T 1/1648 156/60 |
| 2013/0264483 | A1 * | 10/2013 | Abenaim | G01T 1/20182 250/363.01 |
| 2015/0078525 | A1 * | 3/2015 | Hofmann | A61B 6/4233 250/394 |
| 2017/0209107 | A1 * | 7/2017 | Park | A61B 6/56 |
| 2017/0307766 | A1 * | 10/2017 | Abenaim | G01T 1/244 |
| 2019/0339402 | A1 * | 11/2019 | Crestani | G01T 1/243 |
| 2020/0408939 | A1 * | 12/2020 | Onouchi | G01T 1/243 |
| 2024/0427032 | A1 * | 12/2024 | Wrege | A61B 6/032 |

* cited by examiner

CT DETECTOR MODULE AND CT DEVICE

CROSS-REFERENCE TO RELATED APPLICATION(S)

The present application claims priority under 35 U.S.C. § 119 to European Patent Application No. 23180925.2, filed Jun. 22, 2023, the entire contents of which is incorporated herein by reference.

FIELD

One or more embodiments of the present invention relates to a CT detector module and/or to a CT device.

BACKGROUND

Modern computed tomography (CT) devices have a gantry with a rotatable frame on which, inter alia, the X-ray source and a detector module for capturing the X-ray radiation are arranged. As a rule, a CT detector module of this kind comprises an X-ray converter element, which has an X-ray sensor layer and optionally a layer arranged underneath with A/D (analog-to-digital) converters. In recent times, electronic integration was an important trend in X-ray converter elements. The aim here was to reduce the length of the analog path between the analog X-ray sensor layer and the A/D converters which are conventionally realized as ASICs (Application-Specific Integrated Circuit). In the case of integrating X-ray converters, the analog X-ray sensor layer is formed by a suitable sensor layer, for example a scintillator, in combination with a photodiode, while in the case of (counting) X-ray converters, a direct-converting semiconductor sensor is used. An A/D converter embodied as an ASIC then generates the digital output signal. In both cases, integration of the ASICs in a compact construction, in particular stack formation, together with the analog X-ray sensor layer, brings a significant heat source closer to the X-ray sensor elements of the X-ray sensor layer itself.

Since the X-ray sensor elements react very sensitively to fluctuations in heat, heat management is a critical task in the development of a modern CT detector module. Particular challenges of heat management are keeping the operating temperature of the CT detector module stable, avoiding temperature gradients between the adjacent X-ray converter elements and also reducing the temperature gradients inside each X-ray converter elements. These challenges are even more important in the case of counting X-ray converters since the direct-converting semiconductor sensors are additional heat sources and their sensor performance simultaneously reacts very sensitively to thermal changes.

Heat management is currently guaranteed in that a thermal interface between the X-ray converter element and the metal frame of the CT detector module is produced by a heat-conducting adhesive or a heat-conducting paste. Consequently, however, it is not possible to transport a defined quantity of heat since the quality of the thermal interface depends on different factors which cannot be effectively influenced, in particular the thickness of the gap between the X-ray converter and the metal frame, as well as the accurate distribution of the heat-conducting paste.

SUMMARY

It is an object of one or more embodiments of the present invention to provide a CT detector module in which the heat energy can be dissipated as effectively as possible from the X-ray converter element, in particular into a module carrier. It is a further object of one or more embodiments of the present invention to provide a CT detector module in which the temperature gradients inside an X-ray converter element as well as between adjacent X-ray converter elements is reduced compared to the prior art.

One or more embodiments of the present invention achieve at least this object with a CT detector module and a CT device as claimed.

One or more embodiments of the present invention provide a CT detector module which comprises at least one X-ray converter element which has an upper side and a lower side, wherein at its upper side the X-ray converter element has an X-ray detector layer and at its lower side is secured to a heat-conducting module carrier. The X-ray converter element is in heat-conducting contact with at least one metal element, and the at least one metal element is in heat-conducting contact with the module carrier.

In the inventive CT detector module the thermal contact between the X-ray converter element and the module carrier is therefore produced by metal-to-metal contacts which therefore have high heat conductivity. The metal-to-metal contact is produced between the X-ray converter element and an intermediate element made of metal, the metal element, and, further, between this metal element and the module carrier. The module carrier can be, in particular, a metal frame with convection cooler elements, such as cooling ribs. Use of the at least one metal element makes it possible to accurately define the thermal interface between the X-ray converter element and the module carrier since the metallic contact points can accurately fixed. The metal-to-metal heat-conducting contacts are preferably embodied without gaps in order to achieve optimally high heat conduction. The metal-to-metal contacts can be produced after the CT detector module has been secured, for example glued, in particular with UV adhesive, to the module carrier with the required accuracy. In many cases it is possible to improve the thermal contact further by, for example, heat-conducting pastes or pads or adhesives or solder materials in order to increase the thermal contact.

According to one embodiment, the metal element is not a solder. In particular, the metal element is a dimensionally stable element which can assume the form, for example, of a spring, a sheet, a pin, a screw, a spring element or the like.

In advantageous embodiments of the present invention the heat from each X-ray converter element is dissipated not just at one location but at a plurality of locations of the lower side and/or in a planar manner. Here, "planar" is intended to mean that the contact does not just take place point-wise but over a larger area of the lower side of the X-ray converter element, for example over an area of 10%-90%, preferably 20%-80%, more preferably 30%-60% of the lower side of the X-ray converter element.

On its upper side the X-ray converter element has an X-ray detector layer. This faces the X-ray source and is configured to detect the X-rays. The X-ray detector layer can comprise a direct-converting (semiconductor) X-ray sensor layer, for example having CdTe, CdZnTe, CdTeSe, CdZnTeSe, CdMnTe, GaAs, Si or Ge as the semiconductor material. The X-ray detector layer can also comprise a suitable sensor layer which converts X-ray radiation into light, and optically coupled photodiodes, in particular one or more photodiode array(s). Scintillator material, for example GOS (Gd2O2S), CsJ, YGO or LuTAG, is frequently used as the material. The X-ray detector layer can also comprise a layer with analog-to-digital converters to which the X-ray sensor layer is applied, it being possible for the A/D converter layer to be realized in one or more ASIC(s). The X-ray detector layer can be applied to a base plate, also called a substrate, for example a printed circuit board or a ceramic or glass substrate, which then forms the lower side of the X-ray converter element. The X-ray converter element is secured at its lower side to a heat-conducting module carrier.

The module carrier is made, in particular, of metal, for example diecast aluminum. The module carrier can be embodied for mechanical fixing of a respective detector module in a CT device comprising the detector module. For this, appropriate fixing mechanism, device and/or means and aligning mechanism, device and/or means can be provided on the module carrier. The module carrier is preferably embodied as a metallic heat sink which is embodied for the temperature stabilization of the detector module and the removal of heat from the X-ray converter element. For example, the module carrier can be fitted with suitable cooling ribs. The CT detector module is typically part of a rotating gantry of a CT device.

The X-ray converter element can be secured to the module carrier by way of an adhesive, for example a UV adhesive, with other securing means, such as screws, also being possible. A plurality of X-ray converter elements can also be secured to the module carrier so it is thereby “tiled” by the side-by-side mounting of the X-ray converter elements.

One or more embodiments of the present are also wherein heat generated in the X-ray converter element and, in particular, in the X-ray detector layer is efficiently dissipated into the module carrier via a new metal element.

According to a preferred embodiment, the lower side of the X-ray converter element, which is in heat-conducting contact with the at least one metal element, is at least partially provided with a metallic covering. It is consequently possible to improve the heat conduction onto the module carrier and optionally produce large-area contact with the metal element, whereby the heat conduction onto the module carrier is improved still further. The metallic covering can be formed, for example, by a coating with a metal with good heat conduction, for example gold, silver or copper. The metallic covering can be what is known as a “metallized thermal pad”, a metallized heat-conducting pad. The heat-conducting covering can cover some or also all of the lower side of the X-ray converter element, in particular it is provided at the location at which the metal element abuts the X-ray converter element. The metallic covering can be connected by metallized through-holes in a base plate and/or the A/D converter layer of the X-ray detector layer to the A/D converter layer and/or the X-ray sensor layer so the heat can be dissipated from there the into the metallic covering. This is also referred to as thermal via technology. The metallized through-holes can be, for example, contact holes in the base plate.

According to one embodiment, the at least one metal element has a planar metal element, in particular metal sheet, which in a first region abuts the lower side of the X-ray converter element and in a second region abuts the module carrier. The embodiment as a planar metal element is favorable during production and guarantees excellent heat conduction, in particular if at planar regions on its upper and/or lower side(s) the metal sheet abuts elements to be connected. The planar metal element can have, for example, two legs, of which the one leg abuts the lower side of the X-ray converter element and the other leg abuts the module carrier, it being possible for the two legs to form, for example, an angle of about 90°. The metal sheet can therefore be L-shaped or T-shaped in cross-section. The metal element can also have a profile element which can likewise have two legs. The second leg can be arranged in a recess of the module carrier and optionally be secured there, for example by a securing element such as a screw. The recess can be, for example, a gap into which the second leg of the metal element is inserted. In another embodiment the metal element, in particular metal sheet, forms a disc which is inserted between the lower side of the X-ray converter element and the upper side of the module carrier and thus contact with its upper side is in heat-conducting contact with the X-ray converter element and with its lower side, with the module carrier. A securing mechanism, device and/or means or spring elements can be provided in this embodiment too, and these ensure that contact is established. A metal sheet of this kind can also be just one of a plurality of heat-conducting metal elements, in particular the securing device can also be made of metal and thus form part of the heat bridge.

According to one embodiment, the at least one metal element has a spring element which is pressed on the lower side of the X-ray converter element by a restoring force. The spring element can be formed from a metal sheet and have the properties which were described above. For example, an L-shaped, pre-bent metal sheet with prestress can be arranged between the X-ray converter element and the module carrier such that it presses against the lower side of the X-ray converter element. The embodiment in which the metal element has a metal sheet or a spring element are particularly advantageously combined with the embodiment in which the lower side of the X-ray converter element is provided at least partially with a metallic covering. The part provided with the covering can constitute, for example, 20%-80%, preferably 40%-60%, of the lower side of the X-ray converter element.

The spring element can be used as an insert in the module carrier, in particular in a recess of the carrier. When assembling the CT detector module, the X-ray converter element can be glued to the module carrier in a first step, preferably with optimum positional accuracy. A fast-curing adhesive, such as UV adhesive, can be used in this case. Preferably, the spring element or metal sheet is already inserted in the module carrier on gluing, although in certain embodiments it can also be inserted from the side after the gluing process.

The metal-to-metal surface contact can be increased in that the respectively abutting regions are pressed against each other, in particular by a securing element or an element with a restoring force, for example a spring. For example, a screw, for example a grub screw, can be screwed into a hole in a module carrier, which screw extends up to the second region of the metal sheet or the spring element. This region can consequently be pressed onto the module carrier. Furthermore, heat conduction also takes place through the screw itself. Similarly, a further hole can also extend up to the first region of the metal element. A grub screw inserted through this hole can press against the first region of the metal element at the lower side of the X-ray converter element.

Alternatively, at its planar contact regions, at which it should have contact with the lower side of the X-ray converter elements and the module carrier, it is also possible to thermally connect the metal element by way of any desired securing device to these contact regions. The securing device can be, for example, screws, rivets, plunger springs, a solder or also reactive solder. Reactive solder is taken to mean a method in which on the surfaces to be connected, a multi-layer system which, as a rule, is composed of two different metals which are alternately coated one above the other, for example nickel/aluminum, Al/Ti, or Cu/Ag. The heat required for melting the solder is released by a self-propagating exothermic reaction of the multi-layer system. As a rule, the reaction is ignited by an energy pulse, for example by high temperature, mechanical pressure, an electrical spark or laser pulse. In one or more embodiments of the present invention it is therefore possible to apply appropriate reactive solder layers to the regions of the metal element at which it abuts the X-ray converter element and the module carrier. If the CT detector module is put together such that the X-ray converter elements are glued to the module carrier at the provided position, the reaction can be ignited and thus a close metallic connection produced between the metal element and the X-ray converter element as well as the module carrier. The metallic covering on the lower side of the X-ray converter element proves to be advantageous in this embodiment too. Alternatively, the reactive solder can also be ignited as early as before assembly of the X-ray converter elements.

According to one embodiment, the at least one metal element is secured to the module carrier by a securing means. Preferably, the securing device is made of metal and thus likewise forms part of the heat bridge or the metal element. The securing device can be, in particular, a screw, rivet, clamp, a pin or a plunger spring, a solder or also a reactive solder. Preferably, the securing device is a screw which is inserted in a hole in the module carrier and presses against the metal element or the metal element presses against part of the module carrier in order to secure it. In particular, the securing device can be metal screws, for example grub screws.

According to one embodiment, the at least one metal element comprises at least one securing element which is fixed to the module carrier and is prestressed against a metallic covering on the lower side of the X-ray converter elements or against a planar metal element arranged at the lower side of the X-ray converter elements. In this embodiment it is possible for the securing elements to constitute the main heat conductors. The securing elements can be embodied as described above, i.e. as a screw, rivet, clamp, pin or plunger spring. In one embodiment, the securing elements are screws which are screwed into corresponding threaded holes in the module carrier. In particular, these can be holes which extend from below and through the module carrier up to the lower side of the X-ray converter element. The holes can be, for example, perpendicular to the lower side of the X-ray converter element. When metal screws are screwed into these holes, they can extend to the lower side of the X-ray converter element and thus produce thermal contact. When producing the CT detector module, the X-ray converter element can be glued to the module carrier in a first step. Preferably, a metallic covering, which is connected to the heat sources, in particular the X-ray detector layer, preferably by thermal via technology, is located on the lower side of the X-ray converter element. The inserted metal screws or also screws with metallic plunger springs then act as heat-conducting components between the lower side of the X-ray converter element and the module carrier. Metal-to-metal surface contacts can be achieved in that the screws are prestressed against the lower side of the X-ray converter element, in particular against the metallic covering.

According to one embodiment, the at least one metal element is inserted in a recess in the module carrier or is secured to a side wall of the module carrier. The side wall is, in particular, a wall which is at least substantially perpendicular to the upper and lower sides of the X-ray converter element. The recess can accommodate, in particular, a planar metal element, such as a metal sheet. For example, a metal element in the form of a metal block can be secured at one side wall of the module carrier, for example by way of a securing device such as a screw, and this metal block, likewise from below, can rest against the lower side of the X-ray converter element or press against it. The X-ray converter element can in turn be glued to the module carrier in a first step in this connection. The lower side of the X-ray converter element can have a metallic covering which can be connected to the heat sources by thermal via technology. A metal element, which is embodied, for example, as a metal insert or a metal block, can thermally connect the lower side of the X-ray converter element to the module carrier. The metal-to-metal contact is produced in that the metal insert is pressed against the lower side of the X-ray converter element and the metal element is then clamped in this position in the module carrier, for example by a securing device such as a screw. Alternatively, other connecting technologies can also be used in order to keep the metal block in its final position.

According to one embodiment, the at least one metal element is inserted in a recess in the module carrier or secured to a side wall of the module carrier. Particularly high heat conduction is possible because the metal element is inserted in a recess or abuts the side wall. The side wall of the module carrier can be a wall which runs perpendicular to the lower side of the X-ray converter element. The metal element can be presented, for example, as a cuboid so with two adjacent sides it has contact both with the lower side of the X-ray converter element and the module carrier. The recess can be a slit in which a planar metal element is inserted, for example a leg of a metal sheet.

According to one embodiment, the at least one metal element has a reactive solder which heat-conductively connects the lower side of the X-ray converter element to the module carrier. It is possible for the reactive solder to form the metal element. It is also possible, however, for the reactive solder to be used in addition to a planar metal element, for example a metal sheet, which is inserted between the X-ray converter element and the module carrier. In the first-mentioned embodiment the heat-conducting paste is replaced by the soldering technology. Alternatively, a normal solder can be used instead of the reactive solder, and this heat-conductively connects the lower side of the X-ray converter element to the module carrier.

In this embodiment the metallic interface can be realized in that a localized, selective soldering process is carried out which connects the lower side of the X-ray converter element and, if present, a metallic covering arranged there, to the metal surface of the module carrier. In this embodiment the entire X-ray converter element can be glued in a first step, again with high positional accuracy, to the module carrier. Preferably one or more location(s) is/are provided with a metallic covering on the lower side of the X-ray converter element, and these locations can preferably be connected to the heat sources by way of thermal via technology. A selective soldering process can be implemented by device of a reactive solder. When the reactive solder is ignited, a solder joint is directly implemented as a heat-conducting element between the lower side of the X-ray converter element and the module carrier. The igniting of the reactive solder can be triggered by the known ignition technologies, such as laser or heating (for example by way of sparks or flames). Alternatively, a normal solder can be used instead of the reactive solder, and this is introduced either after gluing into the gap between the lower side of the X-ray converter element or the metallic covering arranged there and the upper side of the module carrier. Alternatively, the normal solder can also be inserted into this gap as early as before the gluing step and then merely be heated by way of conventional heating technology, such as lasers or (less preferred) flames in order to produce the metallic connection.

According to one embodiment, at its lower side the X-ray converter element has a base plate which has a recess through which the at least one metal element is in direct heat-conducting contact with the X-ray detector layer. In this embodiment the base plate of the X-ray converter element has a continuous recess, in particular in the center. It can be, for example, a rectangular, round or oval recess which allows the edge elements to be upright. In particular, the recess is embodied as a through-hole so the metal element can be led directly through the recess up to the lower side of the X-ray detector layer. The heat can be removed even more efficiently in this way. The metal element can be embodied as described herein, i.e. for example as a spring element, a metal sheet, metal block, screw, etc. The lower side of the X-ray detector layer is preferably at least partially provided with a metallic covering, for example in the form of a coating or a metallized thermal pad, which can in turn be connected to the X-ray detector layer or the X-ray sensor layer by way of metallized through-holes. The metal element thereby acts as a heat bridge between the X-ray detector layer and the module carrier. The connection between the metal element and the lower side of the X-ray detector layer can be produced, in particular, in the manner described here in respect of the other embodiments. For example, screws can press the metal surfaces against each other. Alternatively, connecting technologies such as reactive soldering can be used in advance or as a final step.

According to one embodiment, at its lower side the X-ray converter element has a base plate, wherein the base plate has, at least in the region in which it is in heat-conducting contact with the at least one metal element, heat bridges between the lower side of the base plate and the X-ray detector layer. The heat bridges can be, for example, metallized through-holes which ensure that the heat flow between the X-ray detector layer and the module carrier is improved. The heat bridges can also be formed by additional metal layers.

One or more embodiments of the present provide a robust and highly efficient heat management concept for the integration of X-ray converter elements in CT detector modules in that consistently gap-free metal-to-metal contacts are used. The heat conductivity is therefore significantly improved with respect to the known solutions with thermal cases or thermal adhesives. The thermal resistance is reduced because gaps are avoided between the individual elements of the CT detector module or these gaps are bridged by the metal element. Improved temperature homogeneity over the entire CT detector module can consequently be achieved with a simultaneously reduced temperature. The signal power and stability is thus improved.

According to one embodiment, at its lower side the X-ray converter element has a base plate which has plated through-holes which form heat bridges between the lower side of the base plate and the X-ray detector layer. The heat conduction is consequently further improved.

According to one embodiment, the module carrier has cooling ribs. This is expedient in order to dissipate the heat introduced into the module carrier to the surrounding air. The temperature of the CT detector module is thus further reduced.

One or more embodiments of the present are also directed toward a CT device which has at least one of the inventive CT detector modules, in particular a plurality of CT detector modules 1 mounted side-by-side along a direction of rotation. All embodiments and advantages cited in respect of the CT detector module are also applicable to the CT device, and vice versa. The CT detector module is, in particular, part of a rotating gantry of the CT device. The CT device can have further conventional components, such as an X-ray source, a patient couch, etc.

BRIEF DESCRIPTION OF THE DRAWINGS

The present invention will now be explained in more detail on the basis of exemplary embodiments with reference to the accompanying drawings.

In the drawings.

Identical parts are indicated by identical reference numerals in the figures.

DETAILED DESCRIPTION

Figure 1:
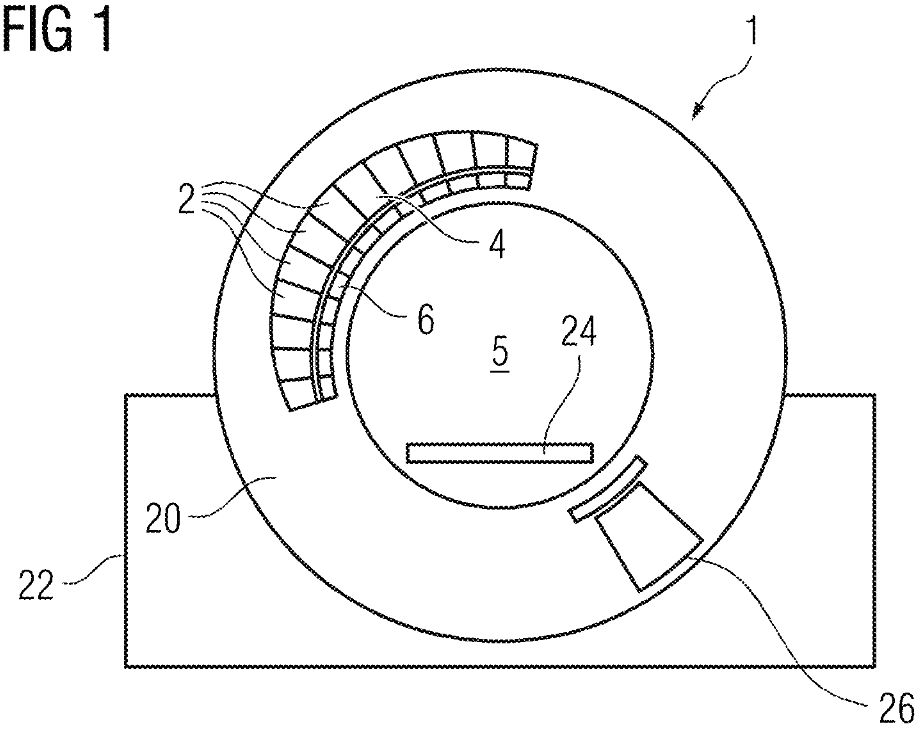
FIG. 1 shows a schematic cross-section through a CT device according to one embodiment of the present invention.

FIG. 1 shows a schematic cross-section through a CT device 1 according to one embodiment of the present invention. According to this, a rotating gantry 20 is supported in a device frame 22. The gantry 20 is configured to rotate around an examination space 5 with a couch 24 on which a patient can be supported. A plurality of detector modules 2 is arranged inside the rotating gantry 20 and these each comprise a module carrier 4 whose side facing the examination space 5 is tiled with X-ray converter elements 6. The X-ray source 26 is situated on the side opposing the CT detector modules 2.

Figure 2:
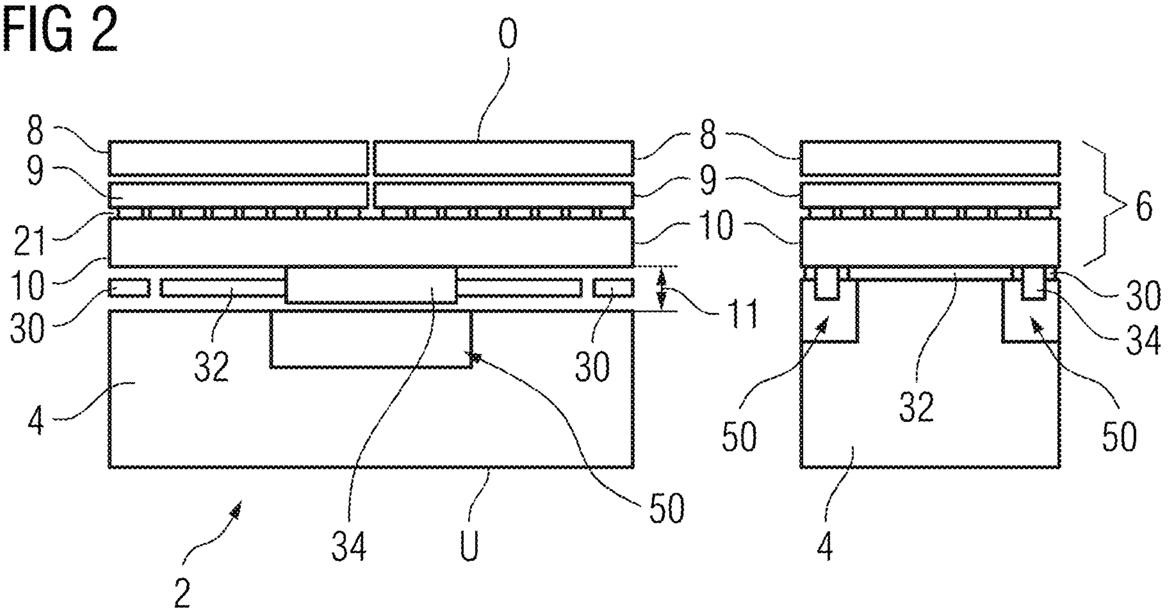
FIG. 2 shows a schematic cross-section in the longitudinal and transverse directions through a CT detector module according to the prior art.

The following images each show a schematic cross-section through a CT detector module 2, and, more precisely, on the left side a section in the longitudinal direction and on the right side a section in the transverse direction. The upper side of the detector module designated by O in the following figures is the side which faces the examination space 5, the lower side designated by U faces away from it. On the left side FIG. 2 schematically shows the sectional representation in an only partially connected state in order to illustrate the glued joint, whereas the right side is illustrated in the connected state. As may be seen in FIG. 2, the detector module 2 has one heat-conducting module carrier 4 respectively which is made, in particular, from metal. This can be, for example, a cast part, for example made of an aluminum alloy. Apart from the X-ray converter elements 6, the module carrier 4 can also carry the power supply and also have cooling ribs in order to effectively remove the absorbed heat. At the upper side O the X-ray converter element 6 has an X-ray detector layer 8, 9. The X-ray detector layer comprises the X-ray sensor layer 8 which can be made, for example, from CdTe. Below this is a layer of A/D-converters 9, for example an A/D electrical sensor layer. These portions 9 can be embodied as an ASIC. The X-ray sensor layer 8 and the A/D converter layer are 9 are connected together via electrically conductive connections, for example solder joints. Gaps can also be filled by what is known as an "underfill", i.e. a filler. The filler can have, for example an epoxy bonding, a plastics material, a composite or a (pre-) polymer or other material. A conductive glued joint, for example, can also be provided. The A/D converter layer 9 is connected to a base plate 10 via an interface layer 21 in which, in particular, electrical connections for forwarding the signals from the A/D converter layer are present. The base plate 10 is, for example, a printed circuit board 10, which can act, in particular, as a rewiring layer and will also be referred to hereinafter as a substrate 10. The base plate 10 can also be embodied in a different way, for example as a ceramic substrate or the like. Reference numeral 34 schematically represents a plug-in connector via which the data processed in the base plate 10 can be removed. In this case, for example a ribbon cable is plugged in the plug-in connector 34. This can be provided on only one side of the detector module 2. Represented here is a two-sided arrangement of plug-in connectors 34. In addition, the module carrier 4 can have recesses 50 which allow facilitated placement of the plug-in connection. The recesses 50 in the module carrier 4 are not represented in the following FIGS. 3 to 8 for the sake of clarity, but can be similarly present. Apart from an implementation shown here via a plug-in connector 34 in combination with recesses 50, other implementations can also be provided and, in particular, arrangements on the detector module 2, which enable removal of the data from the substrate 10 and which, for example, do not render any recesses 50 necessary. The module carrier 4 can be, for example, a diecast aluminum part.

FIG. 2 shows the prior art according to which the X-ray converter element 6 is secured to the module carrier 4 at 30 with the aid of an adhesive, for example a UV adhesive. These adhesive joints 30 can each be arranged at the outer edges of the X-ray converter elements 6. A heat-conducting paste or a heat-conducting adhesive 32 is used therebetween which is arranged in the adhesive gap 11 between the substrate 10 and the module carrier 4. However, this has the drawback that the quantity of the heat-conducting paste 32 and the gap width 11 can vary owing to manufacturing tolerances and the gap filling therefore represents a thermal connection of varying strength. Further, the heat paste 32 can be partially pressed out of the gap 11 during manufacture if, for example, the volume of adhesive is large and the gap is small, whereby the heat conduction between the X-ray converter elements 6 and the module carrier then worsens uncontrollably. A plurality of X-ray converter elements 6 can be glued in a planar manner to a module carrier; reference is also made to the module carrier being tiled. A base plate 10 can also extend, for example. over a plurality of X-ray converter elements 6 or be assigned to just one respectively.

The aim of one or more embodiments of the present invention is to improve the heat bond between the X-ray converter elements 6 and the module carrier 4. This occurs, in particular, by way of an increase and better adjustability of the heat transport via the adhesive gap 11 between the X-ray converter element 6 and the module carrier 4.

Figure 3:
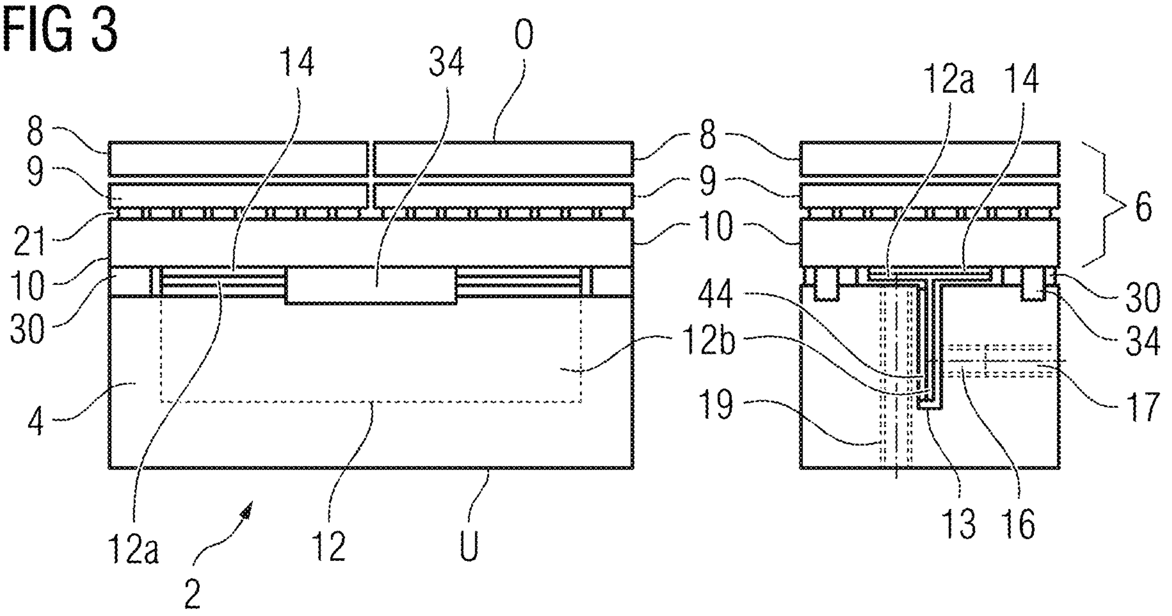
FIG. 3 shows a cross-section in the longitudinal and transverse directions through a CT detector module according to a first embodiment of the present invention.

FIG. 3 represents a first embodiment of the present invention. Firstly, the lower side of the substrate 10 is provided with a metallic covering 14 in this case, for example in the form of a coating or a metallized thermal pad. This has the function of enlarging the surface via which heat from the X-ray converter element 6 can be given off to the module carrier 4 and/or of improving the heat conduction. The metallic covering can also be distributed in a plurality of subareas over the lower side of the X-ray converter element, for example in the form of a plurality of coated surface portions or a plurality of thermal pads. The metallic covering can be, for example, a gold layer. The thickness of the metallic coating can be, for example, 0.5 μm-20 μm, preferably 1 μm-10 μm. The metallic covering 14 can be connected to the upper layers 8, 9 of the X-ray converter element in particular by thermal via technology. However, there can also be embodiments without such a metallic covering. A heat-conducting connection by thermal via technology can result in improved heat conduction from the upper layers 8, 9 even without a metallic covering. Furthermore, the detector module 2 has a new metal element 12 which, as illustrated on the right side, is inserted in a recess 13 in module carrier 4. In the example shown this is a planar metal element in a T-shape which has a leg **12*a* which is arranged parallel to the upper side of the sensor layer and abuts the lower side of the substrate or the metallic covering. The other leg 12*b* is inserted in the recess 13 and has contact with the module carrier 4 here. The module carrier 4 can, as illustrated on the right side, likewise be provided on the contact surface with the metal element 12 with an optional metallic covering 44, for example a gold layer, which improves the heat conductivity even further. The metal element 12 can initially be loosely inserted in the recess 13; initially it still has play. In order to ensure that the metal element 12 is pressed with its leg 12*a* against the lower side of the X-ray converter element 6 and with its leg 12*b* against the module carrier 4, as illustrated on the right side, grub screws 16 can be used which can be introduced into corresponding threaded holes 17, 19. The hole 17 extends, for example, from the side of the module carrier 4 up to the recess 13, so the grub screw 16 inserted therein presses uniformly and in a planar manner against the opposing side of the recess 13, and thus against the module carrier 4, on tightening of the leg 12*b* of the metal element. A second threaded hole 19 leads from the lower side of the module carrier 4 up to the lower side of the substrate 10, so a grub screw (not represented) inserted therein presses the leg 12*a* of the metal element against the lower side of the substrate or against the metallic covering. Uniform and planar thermal coupling is therefore guaranteed at this location too. The metal element 12 can also be L-shaped, for example be embodied as a bent metal sheet. In this case it can also be embodied as a spring element, i.e. with a prestress, with the aid of which is presses against the lower side of the substrate 10. The pre-fixing and mechanical alignment of the X-ray converter element 6 on the module carrier 4 also occurs by way of adhesive 30, for example adhesive joints made of UV adhesive, in the embodiments of FIGS. 3 to 8**. A different fixing can also be implemented, however, for example by screws.

Figure 4:
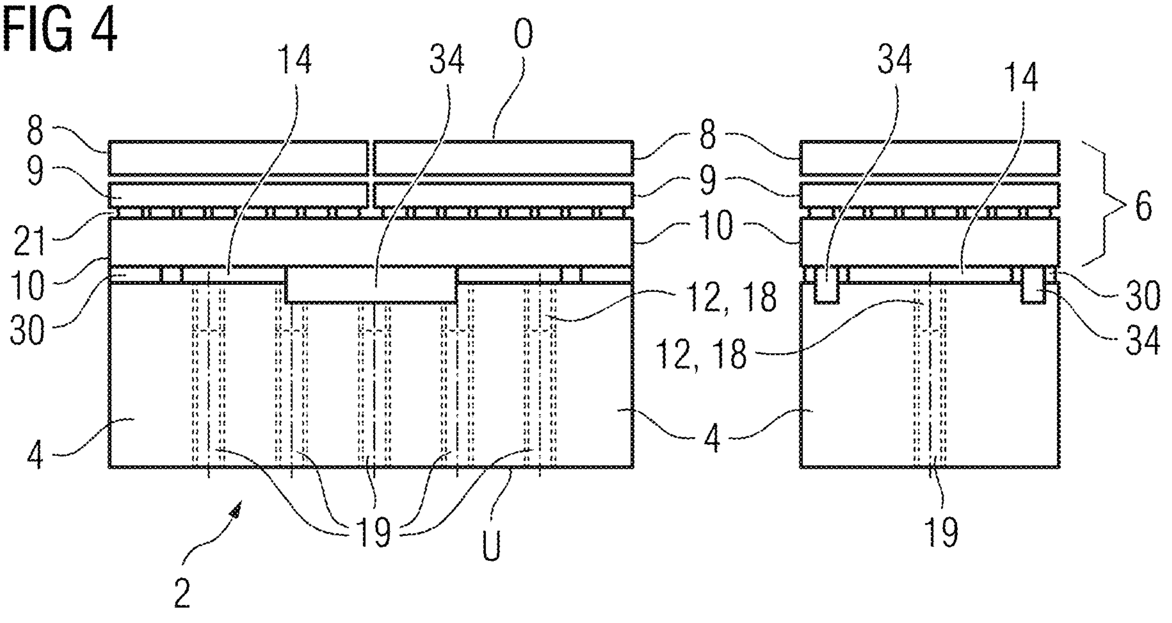
FIG. 4 shows a cross-section in the longitudinal and transverse directions through a CT detector module according to a second embodiment of the present invention.

FIG. 4 shows a further embodiment in which the heat-conducting metal element 12 is substantially formed by securing mechanism, device and/or means 18, in this case grub screws 18, which are screwed into corresponding threaded holes 19 in the module carrier 4 until they press against the lower side of the substrate 10.

In this embodiment the X-ray converter elements 6 can initially be glued to the module carrier 4 with adhesive 30. Preferably, a metallic covering 14 is present at the lower side of the substrate 10 in this embodiment too, at least at the positions of the threaded hole 19. After gluing and curing, grub screws 18 or also screws with metallic plunger springs are inserted in the holes 19 and then act as heat-conducting elements between the lower side of the substrate 10 and the module carrier 4. Metal-to-metal contact is produced in the process by pressing the securing device 18 against the metallic covering 14. In variants a further planar metal element can also be inserted as part of the metal-to-metal contact between the lower side of the X-ray converter element 6 and the upper side of the module carrier 4 and with its upper side is thus in heat-conducting contact with the X-ray converter element 6 and with its lower side with the module carrier 4. The securing device 18 then ensure by way of pressing that the contact is produced and effective heat transport into the module carrier is guaranteed.

Figure 5:
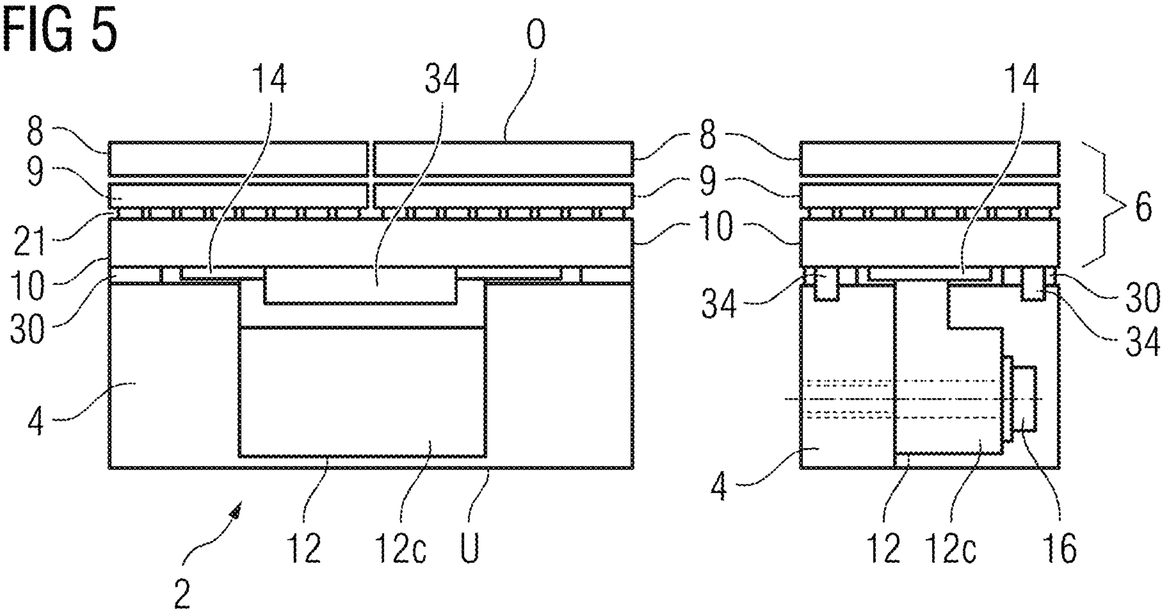
FIG. 5 shows a cross-section in the longitudinal and transverse directions through a CT detector module according to a third embodiment of the present invention.

FIG. 5 shows a further embodiment in which the heat-conducting metal element 12 is formed by a block-like insert 12*c*. This presses from the side against the module carrier 4 and is held in position by a screw 16. As an alternative to the screw, other connecting techniques, for example with a clip, can be used in order to keep the metal element 12 in contact with the lower side of the substrate or the metallic covering 14 optionally applied there. The X-ray converter element 6 is held on the module carrier 4 by an adhesive 30 in this embodiment too.

Figure 6:
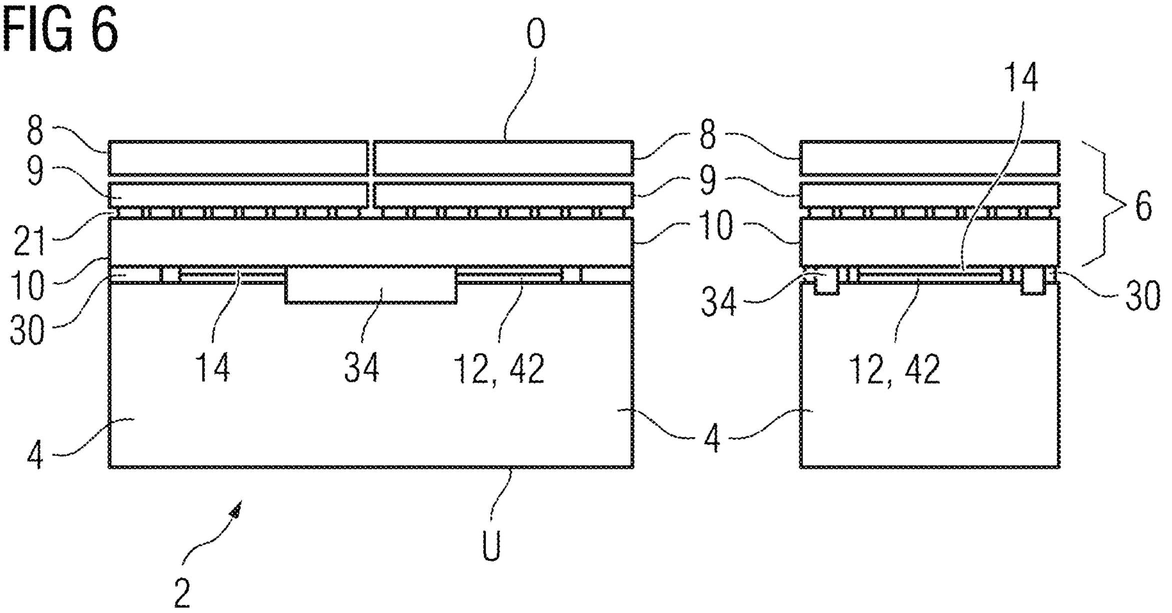
FIG. 6 shows a cross-section in the longitudinal and transverse directions through a CT detector module according to a fourth embodiment of the present invention.

FIG. 6 shows yet a further embodiment in which the metal element 12 is realized by a layer 42 between the substrate 10 and the module carrier 4, or an optional metallic covering 14. This can be a solder. The solder can be introduced into the gap 11 before the X-ray converter element 6 is glued to the module carrier 4. After gluing, the solder can then be melted, for example by way of heating or laser. Alternatively, the layer 42 can also be formed by a reactive solder layer, which then merely has to be ignited and due to an exothermic reaction does not require a further supply of heat. A direct metal-to-metal connection between the lower side of the X-ray converter element and the module carrier 4 is also consequently possible. A metal coating 14 on the lower side of the substrate is not necessary with this glued bonding.

Figure 7:
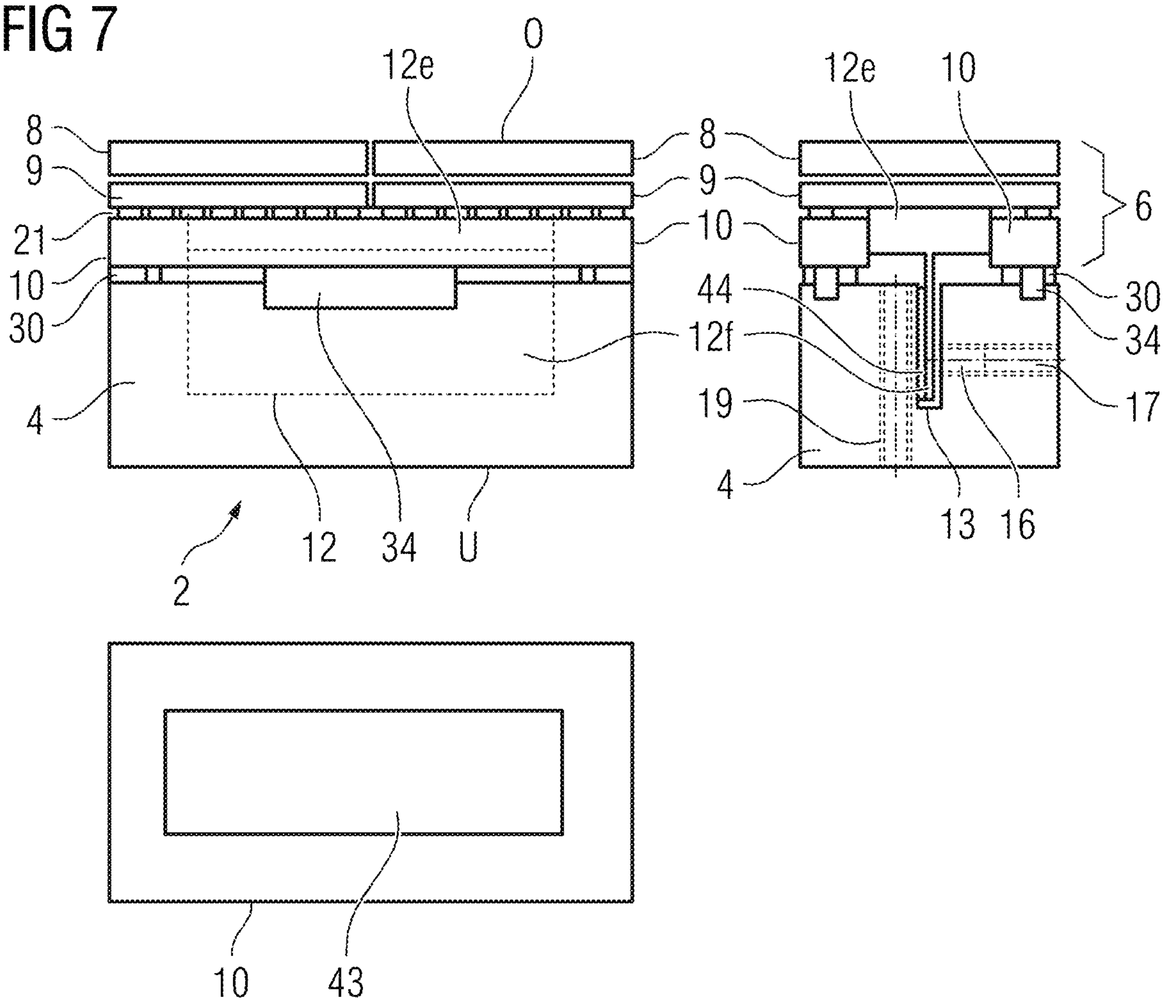
FIG. 7 shows a cross-section in the longitudinal and transverse directions through a CT detector module according to a fifth embodiment of the present invention.

FIG. 7 shows a further embodiment, wherein apart from the sectional depictions, a top view of the substrate 10 without the electrical connecting points of the layer 21 is also represented. In this embodiment the metal element 12 has direct contact with the A/D converter layer 9 over the region 12*e*, and is thus closer to the heat sources in the X-ray detector layer 8,9. This is achieved in that the substrate 10 has a continuous recess 43 through which the metal element 12 extends.

The heat can consequently be removed even more efficiently since the metal element 12 can absorb it closer to the heat sources. The substrate 10 then has an annular construction. The metal element 12 can be embodied in a manner similar to that in the embodiment of FIG. 3, i.e. as a T-shaped metal element whose one leg 12*e* presses on the lower side of the A/D converter layer and whose other leg 12*f* is received in a recess 13 of the module carrier 4. The metal element 12 is pressed by grub screws 16, which are inserted in threaded holes 17 and 19, against the corresponding surfaces, i.e. against the lower side of the A/D converter layer 9 and the side wall of the recess 13 in order to ensure a metal-to-metal surface contact. As an alternative to the grub screws 16, a reactive solder can also be used. Furthermore, a metallic covering can be provided on the A/D converter layer 9 here too in order to achieve further improved heat conduction.

Figure 8:
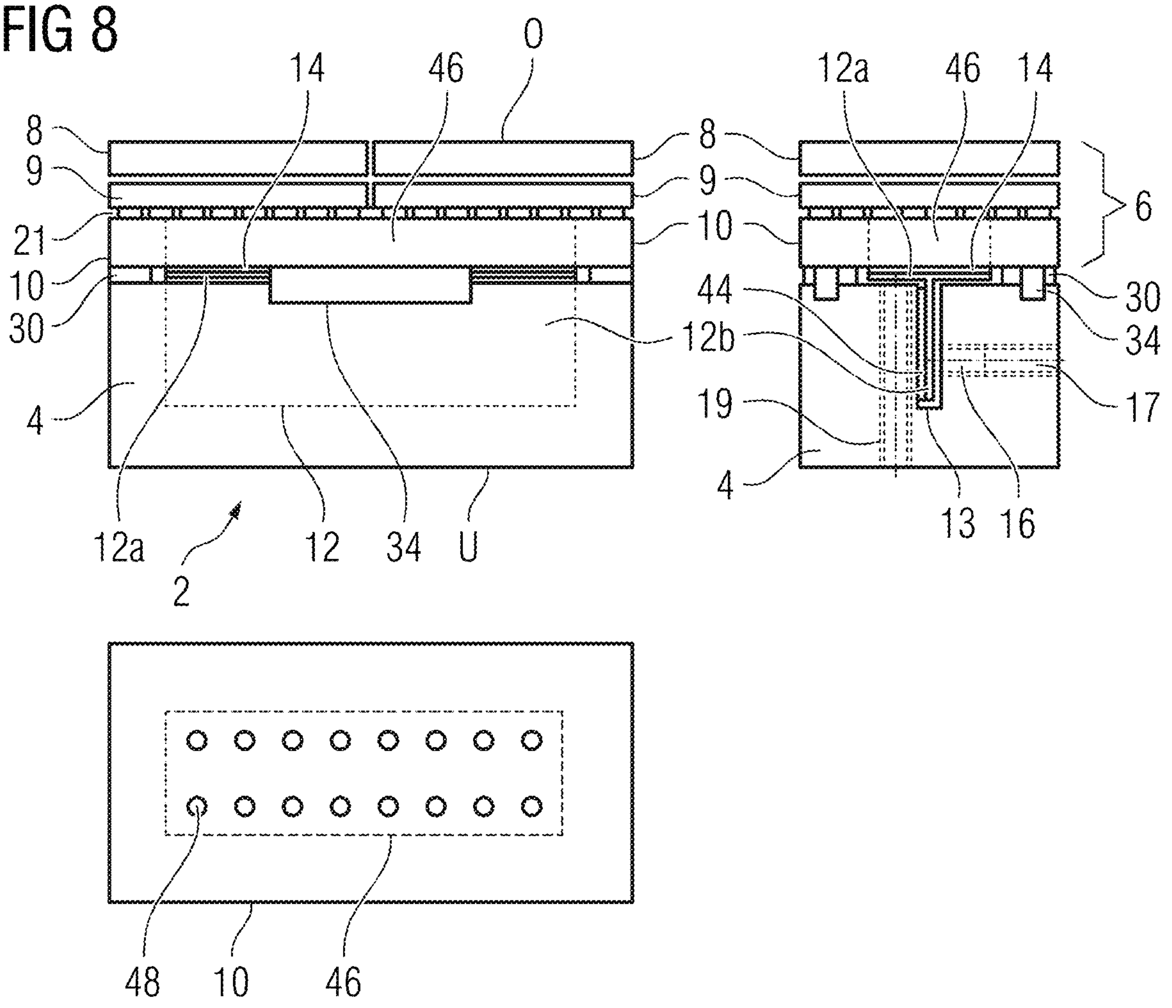
FIG. 8 shows a cross-section in the longitudinal and transverse directions through a CT detector module according to a sixth embodiment of the present invention.

FIG. 8 shows a further embodiment which is similar to the embodiment of FIG. 3 since a T-shaped metal element 12 with legs 12*a*, 12*b* is used here too, which element is inserted in a recess 13 in the module carrier 4. In this embodiment the substrate 10 has a heat-conducting region 46, however, in this case it is situated in the center of the substrate. The bottom illustration in FIG. 8 shows the base plate 10 without the electrical connecting points of the layer 21. The heat flow between the sensor elements 8 and the module carrier 4 is improved further by the thermally conductive layer 46. This can be guaranteed, for example, in that additional metal layers and/or metallized through-holes 48 are present in the thermally conductive region 46.

Independent of the grammatical term usage, individuals with male, female or other gender identities are included within the term.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A CT detector module, comprising:

at least one X-ray converter element having an upper side and a lower side, wherein the at least one X-ray converter element has an X-ray detector layer at the upper side, the at least one X-ray converter element is secured to a heat-conducting module carrier at the lower side, the at least one X-ray converter element is in direct heat-conducting contact with at least one metal element, and the at least one metal element is in direct heat-conducting contact with the heat-conducting module carrier, wherein the at least one metal element has a spring element, which is pressed into direct contact with the lower side of the at least one X-ray converter element by a restoring force.

2. The CT detector module as claimed in claim 1, wherein the lower side of the at least one X-ray converter element is provided at least partially with a metallic covering.

3. The CT detector module as claimed in claim 2, wherein the at least one metal element has a planar metal element having a first region abutting the lower side of the at least one X-ray converter element and second region butting the heat-conducting module carrier.

4. The CT detector module as claimed in claim 1, wherein the at least one metal element has a planar metal sheet, the planar metal sheet having a first region abutting the lower side of the at least one X-ray converter element and a second region abutting the heat-conducting module carrier.

5. The CT detector module as claimed in claim 1, wherein the at least one metal element is secured to the heat-conducting module carrier.

6. The CT detector module as claimed in claim 1, wherein the at least one metal element is inserted in a recess in the heat-conducting module carrier or is secured to a side wall of the heat-conducting module carrier.

7. The CT detector module as claimed in claim 1, wherein the at least one metal element comprises:

a solder or reactive solder connecting the lower side of the at least one X-ray converter element in a heat-conducting manner to the heat-conducting module carrier.

8. The CT detector module as claimed in claim 1, wherein the at least one X-ray converter element has a base plate at the lower side, the base plate having a recess through which the at least one metal element is in direct heat-conducting contact with the X-ray detector layer.

9. The CT detector module as claimed in claim 1, wherein the at least one X-ray converter element has a base plate at the lower side, wherein the base plate has heat bridges between a lower side of the base plate and the X-ray detector layer at least in a region in which the base plate is in heat-conducting contact with the at least one metal element.

10. The CT detector module as claimed in claim 1, wherein the at least one X-ray converter element has a base plate at the lower side, the base plate having plated through-holes forming heat bridges between a lower side of the base plate and the X-ray detector layer.

11. The CT detector module as claimed in claim 1, wherein the heat-conducting module carrier has cooling ribs.

12. A CT device comprising:

at least one CT detector module as claimed in claim 1.

13. The CT detector module as claimed in claim 1, wherein the at least one metal element comprises:

at least one securing device fixed to the heat-conducting module carrier, the at least one securing device being prestressed against a metallic covering on the lower side of the at least one X-ray converter element or against a planar metal element arranged at the lower side of the at least one X-ray converter element.

14. The CT detector module as claimed in claim 13, wherein the at least one X-ray converter element has a base plate at the lower side, the base plate having a recess through which the at least one metal element is in direct heat-conducting contact with the X-ray detector layer.

15. A CT detector module comprising:

at least one X-ray converter element having an upper side and a lower side, wherein the at least one X-ray converter element has an X-ray detector layer at the upper side, the at least one X-ray converter element is secured to a heat-conducting module carrier at the lower side, the at least one X-ray converter element is in heat-conducting contact with at least one metal element, the at least one metal element is in heat-conducting contact with the heat-conducting module carrier, the at least one metal element includes at least one securing device fixed to the heat-conducting module carrier, the at least one securing device being prestressed against, and in direct contact with, a metallic covering on the lower side of the at least one X-ray converter element or against a planar metal element arranged at the lower side of the at least one X-ray converter element.

16. The CT detector module as claimed in claim 15, wherein the at least one X-ray converter element has a base plate at the lower side, the base plate having a recess through which the at least one metal element is in direct heat-conducting contact with the X-ray detector layer.

17. The CT detector module as claimed in claim 16, wherein the at least one X-ray converter element has a base plate at the lower side, wherein the base plate has heat bridges between a lower side of the base plate and the X-ray detector layer at least in a region in which the base plate is in heat-conducting contact with the at least one metal element.

18. The CT detector module as claimed in claim 16, wherein the at least one X-ray converter element has a base plate at the lower side, the base plate having plated through-holes forming heat bridges between a lower side of the base plate and the X-ray detector layer.

19. The CT detector module as claimed in claim 15, wherein the lower side of the at least one X-ray converter element is provided at least partially with a metallic covering.

20. The CT detector module as claimed in claim 19, wherein the at least one metal element has a planar metal element having a first region abutting the lower side of the at least one X-ray converter element and a second region abutting the heat-conducting module carrier.

* * * * *